US008126735B2

(12) United States Patent  
Dicks et al.

(10) Patent No.: US 8,126,735 B2
(45) Date of Patent: *Feb. 28, 2012

(54) SYSTEMS AND METHODS FOR REMOTE PATIENT MONITORING AND USER INTERFACE

(75) Inventors: Kent Dicks, Scottsdale, AZ (US); Ralph Kent, Scottsdale, AZ (US); Thomas Crosley, Gilbert, AZ (US); Terry Bartlett, Cave Creek, AZ (US)

(73) Assignee: MedApps, Inc., Scottsdale, AZ (US)

( * ) Notice: Subject to any disclaimer, the term of this patent is extended or adjusted under 35 U.S.C. 154(b) by 807 days.

This patent is subject to a terminal disclaimer.

(21) Appl. No.: 11/877,994

(22) Filed: Oct. 24, 2007

(65) Prior Publication Data

US 2008/0097793 A1    Apr. 24, 2008

Related U.S. Application Data

(60) Provisional application No. 60/862,743, filed on Oct. 24, 2006.

(51) Int. Cl.
*G06F 3/00* (2006.01)
*G06Q 50/00* (2006.01)
*A61B 5/00* (2006.01)

(52) U.S. Cl. .................... 705/2; 705/3; 710/15; 710/16; 600/300

(58) Field of Classification Search .................. 705/2–3; 710/15–16; 600/300

See application file for complete search history.

(56) References Cited

U.S. PATENT DOCUMENTS

| 5,006,699 A | 4/1991 | Felkner et al. |
| 5,673,692 A | 10/1997 | Schulze et al. |
| 5,721,780 A | 2/1998 | Ensor et al. |
| 5,724,985 A | 3/1998 | Snell et al. |
| 5,772,586 A | 6/1998 | Heinonen et al. |
| 5,891,180 A | 4/1999 | Greeninger et al. |
| 5,936,523 A | 8/1999 | West |
| 6,024,699 A | 2/2000 | Surwit et al. |

(Continued)

FOREIGN PATENT DOCUMENTS

AU    2002100889    6/2003

(Continued)

OTHER PUBLICATIONS

Blount et al., "Remote health-care monitoring using Personal Care Connect", IBM Systems Journal, vol. 46, No. 1, pp. 95-113, (2007).

(Continued)

*Primary Examiner* — Lena Najarian
*Assistant Examiner* — Minnah Seoh
(74) *Attorney, Agent, or Firm* — Snell & Wilmer LLP

(57) ABSTRACT

A method according to one aspect of the present invention includes receiving patient information, analyzing the patient information to identify a condition for the patient, and formatting a report based on the patient information and the patient condition. Embodiments of the present invention may be used to monitor any appropriate medical device from essentially any location from which a communications signal can be sent and received. This enables patients to enjoy an active lifestyle by not being tied to medical device monitoring equipment that is difficult or impossible to transport or having to routinely visit health care facilities. Multiple reports can be formatted to include any desired amount and type of information, and can be transmitted selectively to any number of users.

25 Claims, 4 Drawing Sheets

U.S. PATENT DOCUMENTS

| | | |
|---|---|---|
| 6,034,963 A | 3/2000 | Minami et al. |
| 6,093,146 A | 7/2000 | Filangeri |
| 6,302,844 B1 | 10/2001 | Walker et al. |
| 6,336,900 B1 | 1/2002 | Alleckson et al. |
| 6,402,691 B1 | 6/2002 | Peddicord et al. |
| 6,416,471 B1 | 7/2002 | Kumar et al. |
| 6,443,890 B1 | 9/2002 | Schulze et al. |
| 6,443,891 B1 | 9/2002 | Grevious |
| 6,478,736 B1 | 11/2002 | Mault |
| 6,485,418 B2 | 11/2002 | Yasushi et al. |
| 6,579,231 B1 | 6/2003 | Phipps |
| 6,580,948 B2 | 6/2003 | Haupert |
| 6,598,084 B1 | 7/2003 | Edwards et al. |
| 6,625,642 B1 | 9/2003 | Naylor et al. |
| 6,790,178 B1 | 9/2004 | Mault et al. |
| 6,804,558 B2 | 10/2004 | Haller et al. |
| 6,807,965 B1 | 10/2004 | Hickle |
| 6,893,396 B2 | 5/2005 | Schulze et al. |
| 6,903,657 B2 | 6/2005 | Kwoen |
| 6,915,267 B2 | 7/2005 | Jackson et al. |
| 6,957,107 B2 | 10/2005 | Rogers et al. |
| 6,978,182 B2 | 12/2005 | Mazar et al. |
| 7,039,810 B1 | 5/2006 | Nichols |
| 7,044,911 B2 | 5/2006 | Drinan et al. |
| 7,129,836 B2 | 10/2006 | Lawson et al. |
| 7,134,996 B2 | 11/2006 | Bardy |
| 7,154,398 B2 | 12/2006 | Chen et al. |
| 7,156,808 B2 | 1/2007 | Quy |
| 7,161,484 B2 | 1/2007 | Tsoukalis |
| 7,181,017 B1 | 2/2007 | Nagel et al. |
| 7,231,258 B2 | 6/2007 | Moore et al. |
| 7,242,306 B2 | 7/2007 | Wildman et al. |
| 7,265,676 B2 | 9/2007 | Gordon et al. |
| 7,311,666 B2 | 12/2007 | Stupp et al. |
| 7,438,216 B2 | 10/2008 | Ambekar |
| 7,590,191 B1 | 9/2009 | Macrae |
| 7,733,224 B2 | 6/2010 | Tran |
| 7,761,261 B2 | 7/2010 | Shmueli et al. |
| 2001/0005772 A1 | 6/2001 | Kisakibaru |
| 2001/0051787 A1 | 12/2001 | Haller et al. |
| 2002/0029157 A1 | 3/2002 | Marchosky |
| 2002/0072933 A1 | 6/2002 | Vonk et al. |
| 2002/0128804 A1 | 9/2002 | Geva |
| 2003/0009088 A1 | 1/2003 | Korth et al. |
| 2003/0018742 A1 | 1/2003 | Imago |
| 2003/0050539 A1 | 3/2003 | Naghavi et al. |
| 2003/0072424 A1 | 4/2003 | Evans |
| 2003/0088295 A1 | 5/2003 | Cox |
| 2003/0088441 A1 | 5/2003 | McNerney |
| 2003/0095675 A1 | 5/2003 | Marlow et al. |
| 2003/0149593 A1 | 8/2003 | Mok et al. |
| 2003/0216625 A1 | 11/2003 | Phillips |
| 2004/0015132 A1 | 1/2004 | Brown |
| 2004/0078220 A1 | 4/2004 | Jackson |
| 2004/0097796 A1 | 5/2004 | Berman et al. |
| 2004/0100376 A1 | 5/2004 | Lye et al. |
| 2004/0102683 A1 | 5/2004 | Khanuja et al. |
| 2004/0122488 A1* | 6/2004 | Mazar et al. .............. 607/60 |
| 2004/0127775 A1 | 7/2004 | Miyazaki et al. |
| 2004/0152961 A1 | 8/2004 | Carlson et al. |
| 2004/0199056 A1 | 10/2004 | Husemann et al. |
| 2004/0210458 A1 | 10/2004 | Evans |
| 2005/0002341 A1 | 1/2005 | Lee et al. |
| 2005/0004700 A1 | 1/2005 | DiMaggio |
| 2005/0021370 A1 | 1/2005 | Riff et al. |
| 2005/0038680 A1 | 2/2005 | McMahon |
| 2005/0060187 A1 | 3/2005 | Gottesman |
| 2005/0065815 A1 | 3/2005 | Mazar et al. |
| 2005/0070767 A1 | 3/2005 | Maschke |
| 2005/0119580 A1 | 6/2005 | Eveland |
| 2005/0137465 A1 | 6/2005 | Cuddihy et al. |
| 2005/0149358 A1 | 7/2005 | Sacco et al. |
| 2005/0171410 A1 | 8/2005 | Hjelt et al. |
| 2005/0192649 A1 | 9/2005 | Shehadeh et al. |
| 2005/0197545 A1 | 9/2005 | Hoggle |
| 2005/0203775 A1 | 9/2005 | Chesbrough |
| 2005/0234307 A1 | 10/2005 | Heinonen et al. |
| 2005/0240111 A1 | 10/2005 | Chung |
| 2006/0020302 A1 | 1/2006 | Torgerson et al. |
| 2006/0026118 A1 | 2/2006 | Jung et al. |
| 2006/0035669 A1 | 2/2006 | Chuprun et al. |
| 2006/0036134 A1 | 2/2006 | Tarassenko et al. |
| 2006/0063980 A1 | 3/2006 | Hwang et al. |
| 2006/0064320 A1 | 3/2006 | Postrel |
| 2006/0089542 A1 | 4/2006 | Sands |
| 2006/0111079 A1 | 5/2006 | Tischer et al. |
| 2006/0116744 A1 | 6/2006 | Von Arx et al. |
| 2006/0135858 A1 | 6/2006 | Nidd et al. |
| 2006/0142648 A1 | 6/2006 | Banet et al. |
| 2006/0161222 A1 | 7/2006 | Haubrich et al. |
| 2006/0167346 A1 | 7/2006 | Sarel |
| 2006/0200007 A1 | 9/2006 | Brockway et al. |
| 2006/0202816 A1 | 9/2006 | Crump et al. |
| 2006/0205564 A1 | 9/2006 | Peterson |
| 2006/0212316 A1 | 9/2006 | Jackson et al. |
| 2006/0218011 A1 | 9/2006 | Walker et al. |
| 2006/0235280 A1 | 10/2006 | Vonk et al. |
| 2006/0242295 A1 | 10/2006 | Husemann et al. |
| 2006/0253301 A1 | 11/2006 | Simms et al. |
| 2006/0270421 A1 | 11/2006 | Phillips et al. |
| 2006/0293607 A1 | 12/2006 | Alt et al. |
| 2007/0002791 A1 | 1/2007 | Kasprzyk et al. |
| 2007/0004969 A1 | 1/2007 | Kong et al. |
| 2007/0015974 A1 | 1/2007 | Higgins et al. |
| 2007/0016450 A1 | 1/2007 | Bhora et al. |
| 2007/0033072 A1 | 2/2007 | Bildirici |
| 2007/0055552 A1 | 3/2007 | St. Clair et al. |
| 2007/0061167 A1 | 3/2007 | Brown |
| 2007/0073266 A1 | 3/2007 | Chmiel et al. |
| 2007/0078497 A1 | 4/2007 | Vandanacker |
| 2007/0083246 A1 | 4/2007 | Mazar et al. |
| 2007/0135855 A1 | 6/2007 | Foshee et al. |
| 2007/0143398 A1 | 6/2007 | Graham |
| 2007/0188323 A1 | 8/2007 | Sinclair et al. |
| 2007/0239229 A1 | 10/2007 | Masoud et al. |
| 2007/0250130 A1 | 10/2007 | Ball et al. |
| 2007/0253380 A1 | 11/2007 | Jollota et al. |
| 2007/0267475 A1 | 11/2007 | Hoglund et al. |
| 2008/0059239 A1 | 3/2008 | Gerst et al. |
| 2008/0126131 A1 | 5/2008 | Lou |
| 2009/0048865 A1 | 2/2009 | Breazeale, Jr. |
| 2009/0204434 A1 | 8/2009 | Breazeale, Jr. |
| 2011/0093287 A1 | 4/2011 | Dicks et al. |

FOREIGN PATENT DOCUMENTS

| | | |
|---|---|---|
| WO | 00/49549 | 8/2000 |
| WO | WO 02/058307 | 7/2002 |
| WO | 2005079667 | 9/2005 |
| WO | 2005/101279 | 10/2005 |
| WO | 2006/006159 | 1/2006 |
| WO | 2006060669 | 6/2006 |

OTHER PUBLICATIONS

Milenkovic et al., "Wireless sensor networks for personal health monitoring: Issues and an implementation", Computer Communications, 13 pages (2006).

Michael Setton et al., "Bluetooth sensors for wireless home and hospital healthcare monitoring", Cyberfab, 6 pages, date unknown.

Korhonen et al., "Health Monitoring in the Home of the Future", IEEE Engineering in Medicine and Biology Magazine, pp. 66-73 (May/Jun. 2003).

"WHMS—Wearable Health Monitoring Systems", Electrical and Computer Engineering, The University of Alabama in Huntsville, http://www.ece.uah.edu/~jovanov/whrms/, 13 pages.

Hung et al., "Implementation of a WAP-Based Telemedicine System for Patient Monitoring", IEEE Transactions of Information Technology in Biomedicine, vol. 7, No. 2, pp. 101-107 (Jun. 2003).

Lee et al., "Design and Implementation of a Mobile-Care System over Wireless Sensor Network for Home Healthcare Applications", Proceedings of the 28th IEEE EMBS Annual International Conference, pp. 6004-6007 (Aug./Sep. 2006).

Chen et al., "An i-Mode Portable Healthcare Monitor", Proceedings of the Second Joint EMBS/BMES Conference, IEEE, pp. 1851-1852 (2002).

Kuo et al., "Design and Implementation of Internet-Based In-House Healthcare and Home Automation Systems", IEEE, pp. 2944-2949 (2003).
Jovanov et al., "Stress Monitoring Using a Distributed Wireless Intelligent Sensor System", IEEE Engineering in Medicine and Biology Magazine, pp. 49-55 (May/Jun. 2003).
Lubrin et al., "Wireless Remote Healthcare Monitoring with Motes", Proceedings of the International Conference on mobile Business, IEEE Computer Society, 7 pages (2005).
Guo et al., "Implementing a wireless portable healthcare monitoring system for physiological signals", The Institute of Engineering and Technology, 1 page (2007).
Otto et al., "System Architecture of a Wireless Body Area Sensor Network for Ubiquitous Health Monitoring", Journal of Mobile Multimedia, vol. 1, No. 4., pp. 307-326 (2006).
Yu et al., "A Wireless Physiological Signal Monitoring System with Integrated Bluetooth and WiFi Technologies", Proceedings of the 2005 IEEE Engineering in Medicine and Biology 27th Annual Conference, pp. 2203-2206 (2005).
"Body Area Networks—A "Healthy Aims" Projects", Zarlink Semiconductor Inc., 1 page (2007).
"Bionformatics" downloaded from webpage http://en.wikipedia.org/wiki/Bioinformatics on Aug. 2, 2007 (9 pages).
Mintz, "Microsoft Launches Health Records Site," downloaded from webpage http://bz.yahoo.com/ap/071004/microsoft_healthvault.html?.v=1 on Dec. 18, 2007 (3 pages).
"Bluetooth Sig Aims To Improve Healthcare Experience Through Interoperability," downloaded from webpage http://www.bluetooth.com/Bluetooth/Press/SIG/BLUETOOTH_SIG_AIMS_TO_IMPROVE_HEALTHCARE_EXPERIENCE_THROUGH_INTEROPERABILITY.htm (2 pages).
USPTO; Office Action dated Apr. 14, 2010 in U.S. Appl. No. 11/876,689.
USPTO; Office Action dated Apr. 1, 2010 in U.S. Appl. No. 11/876,695.
USPTO; Final Office Action dated Dec. 21, 2010 in U.S. Appl. No. 11/876,695.
USPTO; Office Action dated Apr. 28, 2010 in U.S. Appl. No. 11/876,708.
USPTO; Final Office Action dated Dec. 22, 2010 in U.S. Appl. No. 11/876,708.
USPTO; Office Action dated May 26, 2010 in U.S. Appl. No. 11/876,713.
USPTO; Final Office Action dated Dec. 22, 2010 in U.S. Appl. No. 11/876,713.
USPTO; Office Action dated Mar. 29, 2010 in U.S. Appl. No. 11/876,719.
USPTO; Office Action dated Dec. 22, 2010 in U.S. Appl. No. 11/876,719.
USPTO; Office Action dated Sep. 15, 2010 in U.S. Appl. No. 11/876,725.
USPTO; Office Action dated Apr. 1, 2010 in U.S. Appl. No. 11/876,744.
USPTO; Final Office Action dated Dec. 21, 2010 in U.S. Appl. No. 11/876,744.
Princeton University Wordnet; http://wordnetweb.princeton.edu/perl/webwn?s=event; accessed Dec. 19, 2010.
USPTO; Office Action dated Jan. 26, 2011 in U.S. Appl. No. 12/951,957.
USPTO; Office Action dated Jul. 29, 2010 in U.S. Appl. No. 11/877,493.
USPTO; Final Office Action dated Mar. 18, 2011 in U.S. Appl. No. 11/877,493.
USPTO; Office Action dated Jan. 26, 2011 in U.S. Appl. No. 11/877,541.
USPTO; Office Action dated Aug. 31, 2010 in U.S. Appl. No. 11/877,545.
USPTO; Office Action dated Feb. 9, 2011 in U.S. Appl. No. 11/877,550.
USPTO; Office Action dated Jan. 27, 2011 in U.S. Appl. No. 11/877,573.
USPTO; Office Action dated Jul. 1, 2010 in U.S. Appl. No. 11/877,582.
USPTO; Final Office Action dated Mar. 2, 2011 in U.S. Appl. No. 11/877,582.
USPTO; Office Action dated Aug. 9, 2010 in U.S. Appl. No. 11/877,930.
USPTO; Final Office Action dated Mar. 14, 2011 in U.S. Appl. No. 11/877,930.
USPTO; Office Action dated Apr. 13, 2010 in U.S. Appl. No. 11/877,946.
USPTO; Final Office Action dated Dec. 21, 2010 in U.S. Appl. No. 11/877,946.
USPTO; Office Action dated Apr. 15, 2010 in U.S. Appl. No. 11/877,966.
USPTO; Final Office Action dated Dec. 21, 2010 in U.S. Appl. No. 11/877,966.
USPTO; Office Action dated Sep. 3, 2010 in U.S. Appl. No. 11/876,732.
USPTO; Office Action dated Jan. 21, 2011 in U.S. Appl. No. 12/952,009.
EP; Examination Report dated Jan. 18, 2011 in Application No. 7844567.3.
CN; Office Action dated Dec. 2010 in Application No. 200780048044.X.
CN; Office Action dated Mar. 2011 in Application No. 200780048064.7.
CN; Office Action dated Mar. 2011 in Application No. 200780048047.3.
PCT; International Search Report and Written Opinion dated May 14, 2008 in Application No. PCT/US2007/082161.
PCT; International Preliminary Report on Patentability dated Apr. 28, 2009 in Application No. PCT/US2007/082161.
PCT; International Search Report and Written Opinion dated Oct. 10, 2008 in Application No. PCT/US2007/082253.
PCT; International Preliminary Report an Patentability dated Apr. 28, 2009 in Application No. PCT/US2007/082253.
PCT; International Search Report and Written Opinion dated Jan. 15, 2009 in Application No. PCT/US2007/082284.
PCT; International Preliminary Report on Patentability dated Apr. 28, 2009 in Application No. PCT/US2007/082284.
PCT; International Search Report and Written Opinion dated Nov. 6, 2008 in Application No. PCT/US2007/082158.
PCT; International Preliminary Report on Patentability dated Apr. 28, 2009 in Application No. PCT/US2007/082158.
PCT; International Search Report and Written Opinion dated Feb. 18, 2008 in Application No. PCT/US2007/082351.
PCT; International Preliminary Report on Patentability dated Apr. 28, 2009 in Application No. PCT/US2007/082351.
PCT; International Search Report and Written Opinion dated May 27, 2008 in Application No. PCT/US2007/082358.
PCT; International Preliminary Report on Patentability dated Apr. 28, 2009 in Application No. PCT/US2007/082358.
PCT; International Preliminary Report on Patentability dated Apr. 28, 2009 in Application No. PCT/US2007/082288.
PCT; International Preliminary Report on Patentability dated Apr. 28, 2009 in Application No. PCT/US2007/082292.
How PGP Works, http://www.pgpi.org/doc/pgpintro/.
USPTO; Advisory Action dated Apr. 1, 2011 in U.S. Appl. No. 11/876,689.
USPTO; Final Office Action dated Dec. 22, 2010 in U.S. Appl. No. 11/876,689.
USPTO; Office Action dated Aug. 30, 2011 in U.S. Appl. No. 11/877,573.
USPTO; Office Action dated Oct. 5, 2011 in U.S. Appl. No. 12/939,070.
USPTO; Office Action dated Sep. 15, 2011 in U.S. Appl. No. 11/877,582.
USPTO; Office Action dated Oct. 17, 2011 in U.S. Appl. No. 12/940,930.
USPTO; Office Action dated May 24, 2011 in U.S. Appl. No. 11/876,725.
USPTO; Office Action dated Aug. 31, 2011 in U.S. Appl. No. 12/951,957.
USPTO; Office Action dated Aug. 30, 2011 in U.S. Appl. No. 11/877,550.

USPTO; Office Action dated May 17, 2011 in U.S. Appl. No. 12/940,957.

USPTO; Office Action dated Jan. 26, 2011 in U.S. Appl. No. 11/877,541.

USPTO; Office Action dated Aug. 8, 2011 in U.S. Appl. No. 11/877,541.

* cited by examiner

SYSTEMS AND METHODS FOR REMOTE PATIENT MONITORING AND USER INTERFACE

CROSS-REFERENCE TO RELATED APPLICATION

This application claims priority to U.S. Provisional Patent Application Ser. No. 60/862,743, filed Oct. 24, 2006, the disclosure of which is incorporated by reference in its entirety for all purposes.

STATEMENT REGARDING FEDERALLY SPONSORED RESEARCH OR DEVELOPMENT

Not applicable.

DESCRIPTION OF THE INVENTION

1. Field of the Invention

The present invention relates to systems and methods for monitoring the health and wellness of patients, and more particularly, to systems and methods for remotely monitoring patient health and providing health care services.

2. Background of the Invention

Historically, patient medical care was often provided for in the patient's home or some other environment apart from a clinical setting. Physicians, midwives, or other healthcare providers would make house calls, observe patient symptoms, formulate diagnoses, and provide treatment. As the state of the art of health care evolved over time, the number of house calls made by healthcare professionals diminished. In large part, health care providers conducted fewer and fewer house calls because it became impractical to bring bulky medical diagnosis and test equipment to the patient. Likewise, it was not cost effective or intellectually feasible for patients to purchase and operate the complicated and expensive medical machines in a home setting. Therefore, the health care model changed dramatically, emphasizing patient visits to health care facilities where an assortment of state-of-the-art test equipment would be available to assist doctors in more accurately assessing and treating patients. This meant that patients were now expected to come to the doctor, rather than the other way around.

Innovations in electronics in the last twenty years have made available a large number of more affordable and patient-operable medical devices that obviated, at least in part, the need for the patient to go to a facility each time a medical test or device checkup was required. Size and expense were not the only factors making this possible; since the new devices provided sophisticated processing in smaller form factors, the technical complexity required to operate the devices were reduced to a level that would not overwhelm a layperson's knowledge. Unfortunately, although portable medical devices such as blood glucose meters now allow patients to perform tests outside the context of medical facilities, patients still need to meet with health care providers to discuss the results obtained.

Some medical devices include wireless transmitters for the communication of data to and from the medical device. For medical devices implanted in a patient, such as a pacemaker, wireless communication allows a healthcare provider to monitor the operation of the medical device, and to optionally monitor a patient's biological and biometric information, the patient's behavior, and other information pertinent to the treatment of the patient. However, the manner in which medical devices communicate data varies depending on the type and manufacturer of the device, and therefore, proprietary equipment has been designed to wirelessly communicate with medical devices only on a specific frequency and using a particular data communication protocol based on the type of medical device being used.

To make patient monitoring more convenient, Remote Patient Monitoring (RPM) was developed. Remote Patient Monitoring (RPM) generally refers to monitoring one or more conditions of a patient without requiring the patient to visit a hospital, doctor's office, or other healthcare facility. RPM can increase the efficiency and effectiveness of providing care to patients while reducing costs. RPM can be particularly useful when a patient has a long-term or chronic disease that would otherwise require frequent visits to a healthcare facility and/or where a patient's treatment regimen should be modified based on changed patient conditions that are monitored by one or more medical devices, such as a pacemaker or glucose meter. For example, Type-I Diabetes patients (a lifelong condition) use glucose meters to monitor their blood sugar level to assist in determining when to take insulin—it would be desirable if such information could be quickly, easily, and effectively relayed to a heath care provider for review and analysis.

Conventional RPM generally involves the use of a specific monitoring device installed in a patient's home. The device collects data concerning the patient's condition and relays the data to a healthcare provider. Some conventional systems require a patient to manually enter the data. For example, a diabetes patient using a conventional system for RPM may be required to sample their blood sugar level using a glucose meter, take note of the reading, and then manually enter the level in the conventional system. There are drawbacks with these conventional devices. Because of their complexity and proprietary interfaces, many are very expensive, which reduces the cost-savings benefit of RPM. Additionally, they often require a land-line connection (such as phone or VPN) to transmit data and/or are physically bulky/heavy and therefore difficult to transport. Furthermore, conventional systems are often unable to provide data to healthcare providers quickly where data must be manually entered by a patient, which can reduce the level of benefit the patient receives from RPM.

Conventional remote health care approaches such as RPM systems also lack the capability to provide an integrated remote patient care environment, allowing remote monitoring to be seamlessly combined with analysis of patient information and feedback from health care providers. What is needed, then, is a system to allow health care providers to freely access patient-related health data, enabling the provider to conduct a virtual house call. What is also needed is a system that can receive medical data from a broad range of medical devices and provide for the quick and efficient management and transport of that data to a healthcare provider. What is also needed is a system that provides for transport of patient information as well as communication information between patients, health care providers, and an automated service.

SUMMARY OF THE INVENTION

Methods and systems according to the present invention may operate in conjunction with any number of medical devices and healthcare providers. Data can be received in any format and from any medical device, and processed and directed to any suitable healthcare provider. A method according to one aspect of the present invention includes receiving patient information (such as from a medical device or the patient), analyzing the patient information to identify a condition for the patient, formatting a report based on the patient information and the patient condition, and providing the report to a recipient. The patient condition can be any state, ranking, condition, diagnosis, classification, categorization, or conclusion that can be identified (implicitly or explicitly) from the patient information. The patient condition can be identified from the patient information alone, or in combination with data from other sources. The report can include some or all of the patient information, as well as any other information useful to the patient or another user (such as a healthcare provider). Multiple reports can be formatted to include any desired amount and type of information, and can be transmitted selectively to any number of users.

A system according to another aspect of the present invention includes a processor, a patient interface, a user interface, and a memory coupled to the processor and storing instructions. The processor executes the instructions in the memory to receive patient information using the patient interface, analyze the patient information to identify a condition for the patient, format a report based on the patient information and the patient condition, and provide the report to one or more users using the user interface. Both the patient interface and user interface can include human operators, interactive voice response (IVR) systems, and other systems and devices to allow patients, doctors, nurses, and other users to quickly and efficiently provide and retrieve information remotely. The system allows users such as doctors and nurses to quickly and efficiently view the reports to assess the patient's condition, prescribe treatments for the patient, and ensure the patient is in compliance with those prescribed treatments—all without requiring that the patient visit a healthcare facility.

Embodiments of the present invention may be used to monitor any appropriate medical device from essentially any location from which a communications signal can be sent and received. This enables patients to enjoy an active lifestyle by not being tied to medical device monitoring equipment that is difficult or impossible to transport or having to routinely visit health care facilities. The present invention can be used to monitor, process, and transport any amount and type of data from any medical device to any suitable user, such as a healthcare provider.

The present invention can also be used for a variety of other monitoring purposes. For example, the present invention can be used to monitor a blood alcohol monitor, alcohol breathalyzer, or alcohol ignition interlock device to help insure a driver does not operate a motor vehicle under the influence of alcohol or other substance. The present invention can also be used in conjunction with a Global Positioning System (GPS) or other geolocation device to monitor the position of a patient. The present invention may also be used in a wide variety of military applications, such as remotely monitoring devices tracking the health status of soldiers on a battlefield in real-time in order to quickly dispatch aid to wounded soldiers. The present invention may be used to remotely monitor a chemical, biological agent, or radiation sensor carried by a soldier to detect an attack by unconventional weaponry.

Embodiments of the present invention also provide for processing of the medical data received from patients, such as analysis of patient medical data to identify historical trends and alert a patient and/or health care provider when a certain threshold condition is reached, indicating that action or intervention is required. Other embodiments determine whether patients are in compliance with home health care directives such as operating medical devices or administering prescribed treatments of medications. Still other embodiments relate to determining whether patients are at risk for certain heath issues arising based on interactions of medications with other drugs, supplements, or foods.

Aspects of the present invention also relate to interfaces for patients to access information regarding health care through a health care system interface. Embodiments of the user interface include an interactive voice response system interface, an operator interface, a mobile computer interface, or a mobile telephony interface. Systems and methods for remote patient monitoring according to the present invention provides quick and efficient routing of communications from patients to caregivers so that the patient need not endure a long (and potentially dangerous) wait to discuss a medical issue with a qualified caregiver. This allows more patients to be serviced in less time, and with fewer delays Both the foregoing summary and the following detailed description are exemplary and explanatory only and are not restrictive of the invention.

BRIEF DESCRIPTION OF THE DRAWINGS

A more complete understanding of the present invention may be derived by referring to the detailed description and claims when considered in connection with the following illustrative figures.

DETAILED DESCRIPTION OF EXEMPLARY EMBODIMENTS

Figure 1:
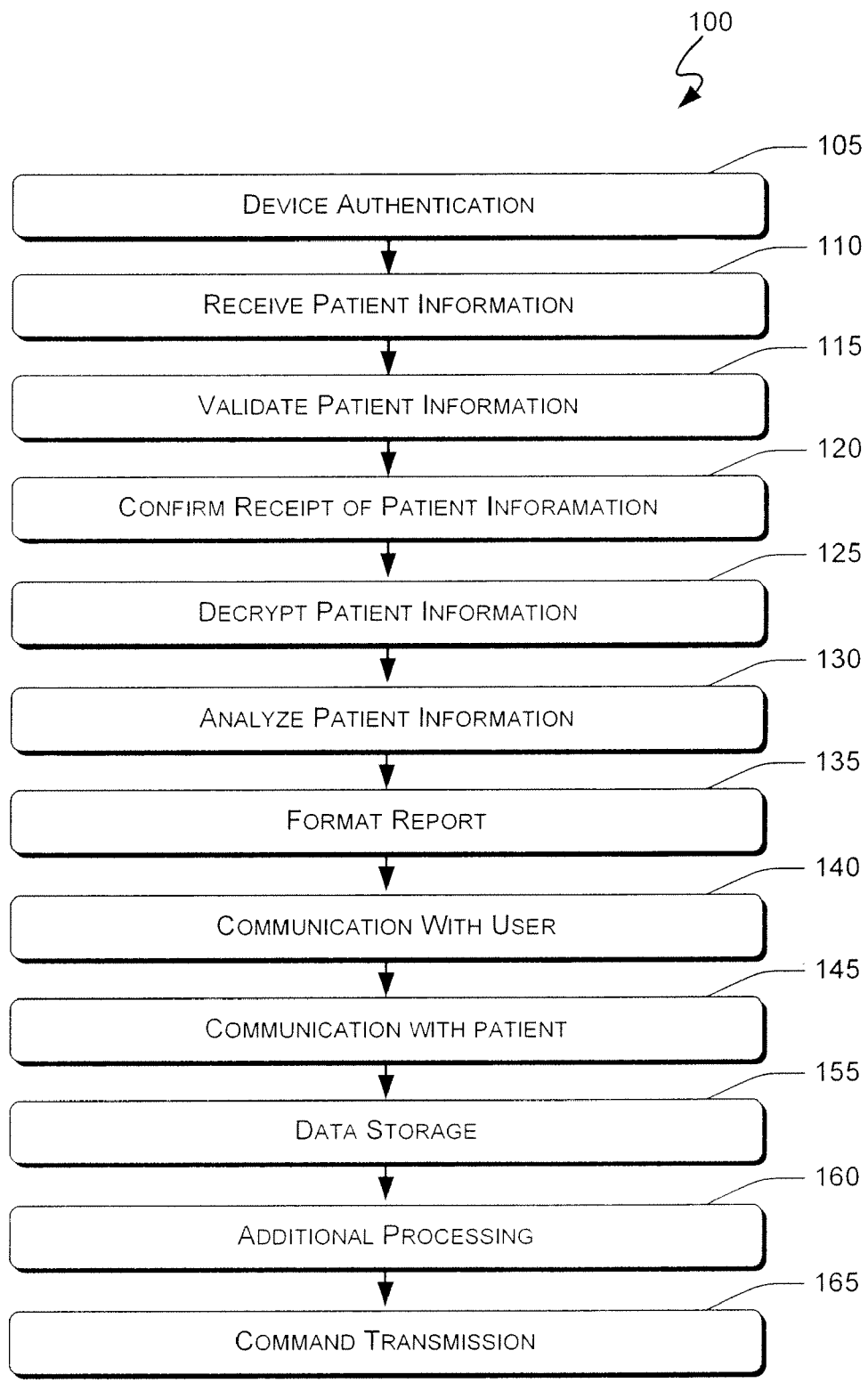
FIG. 1 is a flow diagram depicting an exemplary process for remote patient monitoring according to various aspects of the present invention.

An exemplary method according to an aspect of the present invention is depicted in FIG. 1. In this method, a device providing patient information is authenticated (105), and the patient information is received (110), validated (115), and confirmed (120). Encrypted patient information is decrypted (125). The patient information is analyzed (130) and used to format a report (135). The method provides for the bidirectional communication with one or more users (140) and/or one or more patients (145). Data (including the patient information, report, and other data) may be stored (155). Additional processes can be performed (160) and one or more commands transmitted (165). Any combination and/or subset of the elements of the method depicted in FIG. 1 may be practiced in any suitable order and in conjunction with any system, device, and/or process. The method shown in FIG. 1 can be implemented in any suitable manner, such as through software operating on one or more computer systems. Exemplary systems for performing elements of the method shown in FIG. 1 are discussed later in this description. Throughout this application, the terms "patient information" and "patient data" are used interchangeably.

Device Authentication

One or more devices providing the patient information may be authenticated to achieve any result. For example, a device may be authenticated to restrict receipt of patient information to medical devices and other entities operating as part of the present invention. Authentication can also prevent sensitive medical data from being broadcast and viewed by unintended recipients. A device may also be authenticated to verify the device is able to properly communicate with a medical data server. During authentication, the authenticated device or devices may also be remotely commanded, and such commands may include steps that configure devices to interoperate with components of the present invention. For example, but not by way of limitation, such steps may include the downloading of software applications, applets, embedded operating code, and/or data.

A device can be authenticated in any manner. For example, a device can be authenticated using an authorization code. The authorization code can be any number, code, value or identifier to allow the intermediary device to be identified as a valid provider of the patient information. In one exemplary embodiment of the present invention, an intermediary device providing patient information received from a medical device stores an authorization code and broadcasts the authorization code in response to a request for authorization. Unless the authorization code matches a code stored by the receiver of the patient information (such as a medical data server, remote patient monitoring system, or other suitable entity), the patient information will not be accepted from the intermediary device. Receipt of the patient information from a device, system, or other entity need not necessarily be predicated upon successful authentication, however.

In another exemplary embodiment of the present invention, an intermediary device providing patient information (such as data from a medical device) using a wireless network protocol (such as Bluetooth) is authenticated based on whether the intermediary device advertises one or more services. In this context, advertised services reflect functions, utilities, and processes the intermediary device is capable of performing. The intermediary device broadcasts indicators of this functionality, thus "advertising" them to other systems and devices. In the present exemplary embodiment of the invention, unless the intermediary device advertises a service that is identifiable with the operation of, and retrievable by, the present invention (i.e. a process capable of broadcasting the medical device data to a medical data server, for example), the intermediary device is not authenticated and thus the patient information will not be accepted from the intermediary device.

Receipt of Patient Information

In the exemplary method shown in FIG. 1, patient information is received from one or more entities (110). The patient information can be received using any form of wireless or wired communication protocol or connection. Accordingly, any system implementing the method of FIG. 1 does not need to be physically located at or near the source of the patient information. Patients monitored in accordance with the present invention are thus able to lead active lifestyles without being required to remain physically close to the system(s) collecting the patient information, such as a medical device or an intermediary device that receives data from a medical device. The patient information can be collected (in whole or in part) from any medical device, such as a blood glucose meter, a pacemaker, a blood pressure monitor, an insulin pump, a pulse oximeter, a holter monitor, an electrocardiograph, an electroencephalograph, a blood alcohol monitor, an alcohol breathalyzer, an alcohol ignition interlock, a respiration monitor, an accelerometer, a skin galvanometer, a thermometer, a patient geolocation device, a scale, an intravenous flow regulator, patient height measuring device, a biochip assay device, a sphygmomanometer, a hazardous chemical agent monitor; an ionizing radiation sensor; a monitor for biological agents, a loop recorder, a spirometer, an event monitor, a prothrombin time (PT) monitor, an international normalized ratio (INR) monitor, a tremor sensor, a defibrillator, or any other medical device. A medical device that includes a combination of different medical devices (such as those listed previously) may be monitored in accordance with the present invention. The medical device can be partially or completely implanted in a patient, such as in the case of a pacemaker. The medical device may also be located externally to a patient. The medical device may be connected to a patient (for example, through one or more electrodes), or operate independent of any coupling to a patient, such as a scale. The medical device may also operate in conjunction with a temporary interfacing with a patient, such as the case of the cuff of a blood pressure monitor encompassing the arm of a patient to take a reading.

Figure 2:
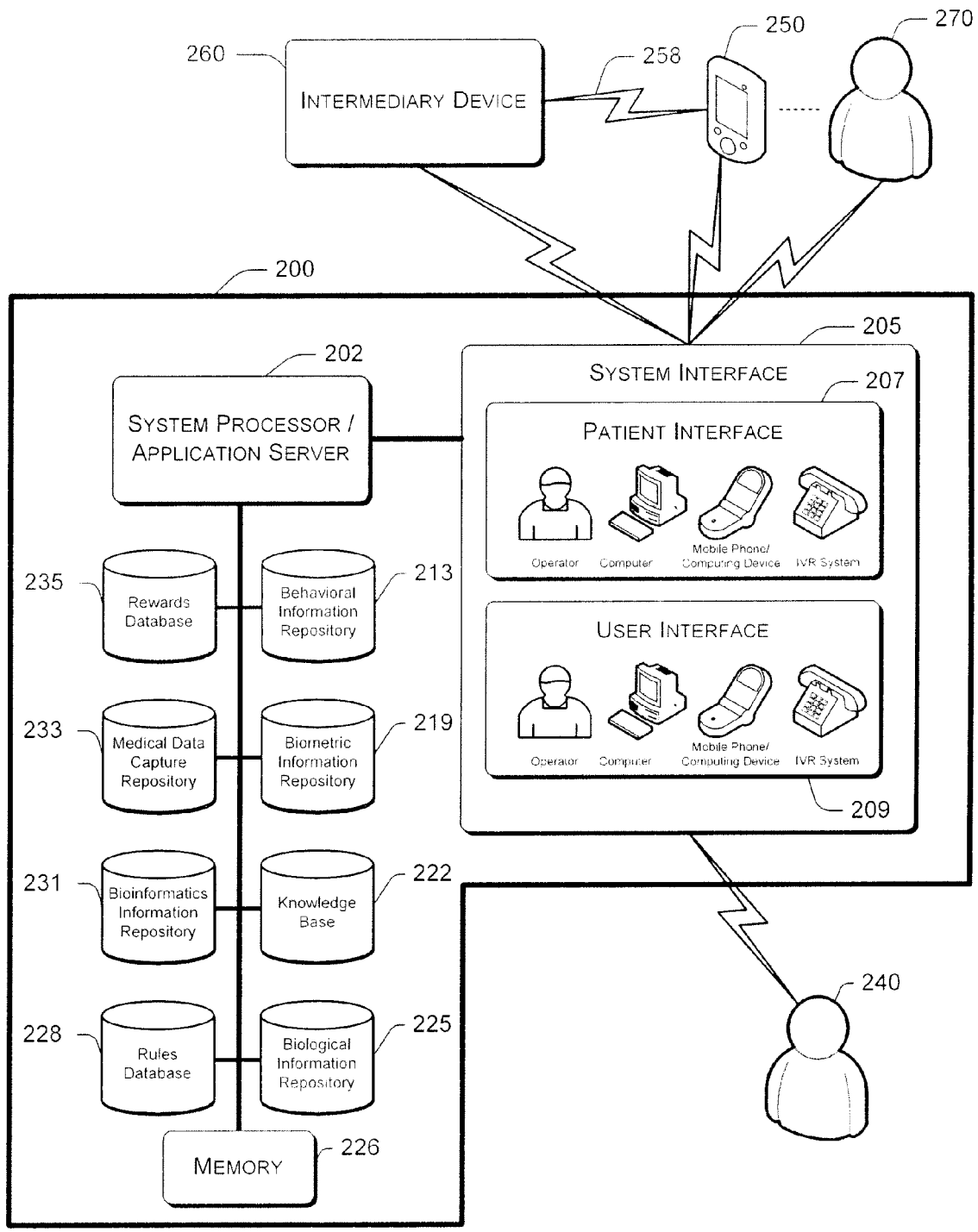
FIG. 2 is a block diagram depicting an exemplary system for remote patient monitoring according to various aspects of the present invention.

The patient information can be received by any person, system, device, or other suitable recipient performing methods for remote patient monitoring in accordance with the present invention. The exemplary method in FIG. 1 may be practiced manually by a human being, automatically by a device, or a combination of the two. An exemplary system for performing the method depicted in FIG. 1 is depicted in FIG. 2 and is discussed in detail below.

In one exemplary embodiment of the present invention, the patient information is transmitted to a medical data server to allow the patient information to be analyzed and processed to identify a condition for the patient. The patient information can be transmitted to a single medical data server, or to a plurality of medical data servers. The medical data server can be any suitable recipient of the patient information. For example, the medical data server can be a computer system or other device as well as a human recipient (such as a doctor, nurse, or other healthcare provider). An exemplary system for remote patient monitoring incorporating an embodiment of a medical data server will be more fully described below in regards to FIG. 2.

The patient information can be transmitted to the medical data server in any suitable manner. For example, the data can be transmitted to the medical data server through a wired connection, such as a telephone line, fiber optic cable, and/or coaxial cable. The data may also be transmitted wirelessly using any suitable wireless system, such as a wireless mobile telephony network, General Packet Radio Service (GPRS) network, wireless Local Area Network (WLAN), Global System for Mobile Communications (GSM) network, Personal Communication Service (PCS) network, Advanced Mobile Phone System (AMPS) network, and/or a satellite communication network. The data may be transmitted using any suitable combination of multiple wired and wireless communication methods. The transmission method selected to transmit the data to the medical data server can be chosen according to any desired criteria. For example, one or more transmission methods can be selected from a plurality of possible transmission methods to send the data based on each method's cost, time required to transmit, reliability, security, or any other suitable factor.

Patient information can be received directly from a medical device. For example, some medical devices such as pacemakers and other devices implanted in a patient include wireless transmitters to wirelessly broadcast data. A medical device can also provide the patient information through a wired or wireless connection using an intermediary device in communication with the medical device. In one embodiment of the present invention, for example, a medical device provides data through a serial port (a wired connection) to a computing device. The computing device is in turn connected to a wireless router. The data can thus be received wirelessly after being retransmitted from the wireless router. The router in this example could also transmit the patient information through a wired Ethernet connection. The patient information may be received in any other manner, such as by an interactive voice response (IVR) system, a mobile computing device, a mobile telecommunication device, a computer system connected to a network, and/or a human operator.

Patient information can be transmitted in any manner. For example, patient information from a medical device (FIG. 2, 250) can be transmitted to a medical data server (FIG. 2, 200) in real-time or near-real-time, or the patient information data can be stored (such as in a memory storage device) for a period of time before being transmitted to the medical data server (200). In some cases, for example, it may be more efficient to transmit accumulated blocks of patient information in batches rather than initiating communication with the medical data server (200) each time patient information is available. In other cases, a medical device or other intermediary device may be temporarily out of range of a communications system, or otherwise unavailable to transmit the patient information on a real-time basis.

The patient information can include data from a plurality of different sources. For example, patient information may include data from a plurality of different medical devices (such as those listed previously), where each medical device may perform any combination of functions. For example, data from a glucose meter, blood pressure monitor, and combination scale/height measuring device each transmitting data in different formats and using different communication protocols may each be received in accordance with the present invention. Any other suitable method for receiving data from a plurality of medical devices may also be used in conjunction with the present invention.

The patient information may include any suitable data collected from any source. For example, the patient information may include the patient's biological and biometric information, the patient's behaviors, results of analysis of physical patient parameters, and information regarding the patient's environment. For example, a medical device such as a glucose meter could provide data regarding a patient's current (or last measured) blood glucose level, the date and time the patient last used the glucose meter, and the current temperature or other environmental factors that might affect a glucose test. Other possible environmental parameters or medical device diagnostic information that may be included in the data received from a medical device include a battery charge level, a temperature, a barometric pressure, a code relating to an accessory for the medical device, a data validity measurement, an elapsed time since a previous reading by the medical device, a test result parameter, a signal-to-noise parameter, and a quality of service (QoS) parameter, and combinations thereof. Data received from a medical device may also include any other suitable information, such as health status information entered by the patient into a medical device or other device operating in conjunction with the present invention.

The patient information may pertain to a single patient or multiple patients. In the case where a single medical device or other source provides medical data or other patient information regarding multiple patients, the data can be identified with an individual patient either in the data received by medical device (such as by using a patient identifier) or through processing in accordance with the present invention. The patient information may include any number of separate data fields and/or measurements.

The patient monitoring may pertain to multiple medical devices of the same type for the same patient, each identified by a unique serial number and tied to the patient's unique patient ID. For example, a child, who is type 1 diabetic, may be required to take readings at both her school during the day and at home. Rather than carry her blood glucose meter and/or associated wireless hub (e.g. cell phone) back and forth every day, the child has one glucose meter and phone at school, and another glucose meter and phone at home. Readings from both sets of meters and hubs (cell phones) get merged together in the database based on the child's patient ID. Another variation is the child has separate glucose meters at both school and home, but they are both tied to the same hub (e.g. cell phone) which she carries back and forth to school in her backpack. Another example of this would be an adult that leaves one glucose meter at work, and has another one at home. The software provided by blood glucose meter manufacturers (such as Lifescan) do not provide for the merging of data from two meters for one patient.

The received patient information may be in any format. Different medical devices from different manufacturers often use different formats for providing data. For example, data from a glucose meter may be provided in a series of fixed-length data records followed by a terminator indicator (such as a null or other predefined character) and/or a checksum for validating the data. Any type of data may be provided. In the case of a glucose meter, the data may include one or more readings of a patient's blood glucose level and the date and time each reading was taken. The medical device identifier discussed previously may be used to determine a specific data format used by a medical device. Alternatively, a data format may be specified by a user or selected by analyzing the format of the data received and comparing it to a set of known medical device data formats. The patient information can also be received through any variety of communication formats, and may be partially or entirely encrypted.

For example, the patient information can be included in a file having a tokenized format such as standard ASCII text format, or any other suitable standardized file format, such as an MS Word document, MS Excel file, Adobe PDF file, or binary picture file (JPEG, bitmap, etc.). The data within such a file can be ordered in any manner and have any suitable delimiters, notations, or other features. For example, a list of multiple glucose level readings in a text file message could be provided chronologically by when the readings were taken, with comma or tab delimiters to denote the start and end of each reading. The message may also have a unique and/or propriety format.

The format of the message can also be based on the method by which the message is transmitted to the medical data server. For example, where the message is transmitted to the medical data server using a wireless mobile telephone such as a cellular phone, the message can be formatted as an SMS text message. Similarly, the message may be formatted as an XML record, email, and/or facsimile. The message can include multiple formats and/or multiple messages may be formatted having different formats for transmission in a variety of methods or to a variety of recipient medical data servers.

Validation of Patient Information

In the exemplary process shown in FIG. 1, the patient information is validated (115). The patient information can be validated in any suitable manner to achieve any result. For example, the patient information may be validated to ensure it was received properly and completely. The patient information may also be validated to ensure it includes data from a particular source, such as from a specific medical device or particular type of medical device. The patient information may also be validated to ensure that fields in the data correspond to predetermined values and/or are within certain thresholds or tolerances. Any number, code, value or identifier can be used in conjunction with validating the patient information. For example, the patient information can be validated by analyzing a medical device serial number, a medical device identifier, a patient identifier, one or more parity bits, a cyclic redundancy checking code, an error correction code, and/or any other suitable feature.

The patient information can be validated in any other desired manner. For example, in one embodiment of the present invention, the patient information is validated by performing an analysis of a subset of the patient information. The subset of information can include any suitable data, such as a medical device serial number, a medical device identifier, a patient identifier, one or more parity bits, a cyclic redundancy checking code, and/or an error correction code. The subset of the patient information is compared to a previously stored patient datum to validate the subset is correct.

Confirmation of the Receipt of Patient Information

In the exemplary process shown in FIG. 1, the receipt of the patient information is confirmed (120). Confirmation of the receipt of the patient information can be performed in any suitable manner to achieve any result. For example, a predetermined acknowledgement signal can be transmitted to the source of the patient information once the patient information is received (110) and validated (115). Alternatively, a predetermined acknowledgement failure signal may be transmitted to the source of the information, whereby the source of the patient information retransmits the information or otherwise corrects the condition that led to the failure to confirm receipt.

Decryption/Decoding of Patient Information

The patient information can be transmitted in any format. For example, the data from the medical device can be transmitted exactly as it is transmitted from the medical device. This would be the case in embodiments of the present invention where the medical device itself is transmitting the data directly to a system implementing methods in accordance with the present invention, such as a medical data server or wellness monitoring system. Alternatively, in embodiments of the present invention where the data is being received from the medical device and retransmitted by one or more intermediary devices, the patient information can be reformatted, modified, combined with other data, or processed in any other suitable manner before being transmitted to a medical data server or wellness monitoring system. For example, the patient information can be encrypted prior to transmission to a medical data server, and this encryption may occur at any stage, for instance in a medical device providing the patient information, or at a stage after being transmitted by the medical device. In cases where the patient information is being combined with other data and transmitted to the medical data server, all of the data may be encrypted or simply a portion of the patient information. In an alternate embodiment, a digest of the patient information may be encrypted, to digitally "sign" the data contents to verify its authenticity. For example, but not by way of limitation, this digest may be produced by providing the received patient information to a hashing algorithm such as the MD5 or SHA-1 Secure Hashing Algorithm as specified in National Institute of Standards and Technology Federal Information Processing Standard Publication Number 180-1.

Asymmetric encryption algorithms and techniques are well known in the art. See, for example, RSA & Public Key Cryptography, by Richard A. Mollin, CRC Press, 2002, and U.S. Pat. No. 4,405,829, issued Sep. 20, 1983, the disclosures of which are fully incorporated by reference for all purposes to the extent not inconsistent with the claims, drawings, or specification herein. In an illustrative example, if two parties (for example, "Alice" and "Bob") wish to communicate securely using public key cryptography, each party begins by generating a unique key pair, where one of the keys is a private key that is kept in confidence by that party, and the other key is a public key that may be publicly distributed, published only to a message recipient, or made available through a public key infrastructure. The key generation step need be done by a party only once, provided that the party's private key does not become compromised or known by another party. If Alice wants to send a message confidentially to Bob, she may use Bob's public key to encrypt the message, and once sent, only Bob can decrypt and view the message using Bob's private key. But if Alice also wanted Bob to have assurance that the message was in fact coming from her, she could further encrypt the message with her private key before sending, then when Bob's private key and Alice's public key are used to decrypt the message, Bob knows for certain that he was the intended recipient and that Alice was the one who originated the message, and Alice knows that only Bob will be able to decrypt and read her message.

Asymmetric cryptography may be utilized to enhance security of certain implementations of the present invention. In an alternate embodiment, data transmitted by a medical device 250 is encrypted with a private key of the medical device user (or optionally with the private key of a health care provider that is operating the medical device), or with a public key of the intended recipient system such as the medical data server 200, or with both keys. The private and/or public keys may be delivered to the medical data server 200 through a wired or wireless connection, allowing the medical data server 200 to be configured for secure operation. In one embodiment, the system or medical data server 200 may request that the public key of the medical device be forwarded to enable decryption of any medical information encoded with the user's private key. In this manner, the data may be authenticated as coming from the actual patient that is desired to be monitored, and optionally, the patient may also be assured that only the intended recipient system or medical data server 200 is capable of decrypting and gaining access to the patient's medical device data (or patient information). The received patient information can be decrypted using a private key associated with the medical data server 200, a public key associated with a user of a medical device, a public key associated with a medical device 250, or combinations thereof.

In alternate embodiment, encrypted or unencrypted data can be transmitted through an encrypted transmission protocol, such as the wireless encryption protocols (WEP, WPA and WPA2) associated with the IEEE 802.11 wireless protocols. Any number of other encryption methods can be used to encrypt the medical device data in conjunction with the present invention. The medical data server 200 may decrypt the patient information to allow processing of the data. To protect the data from unauthorized viewing, an intermediary device could simply retransmit encrypted patient information from another source to the medical data server 200.

Analysis of Patient Information

In the exemplary process depicted in FIG. 1, the patient information is analyzed to identify a condition for the patient (130). The patient condition can be any state, ranking, condition, diagnosis, classification, categorization, or conclusion that can be identified (implicitly or explicitly) from the patient information. The patient condition can be identified from the patient information alone, or in combination with data from other sources. For example, referring to FIG. 2, the patient information may be analyzed in conjunction with data from a Behavioral Information Repository 213, Biometric Information Repository 219, Knowledge Base 222, Biological Information Repository 225, Rules Database 228, Bioinformatics Information Repository 231, Medical Data Capture Repository 233, Rewards Database 235, and/or any other data source. The patient condition may include any amount and type of information in any format.

Figure 3:
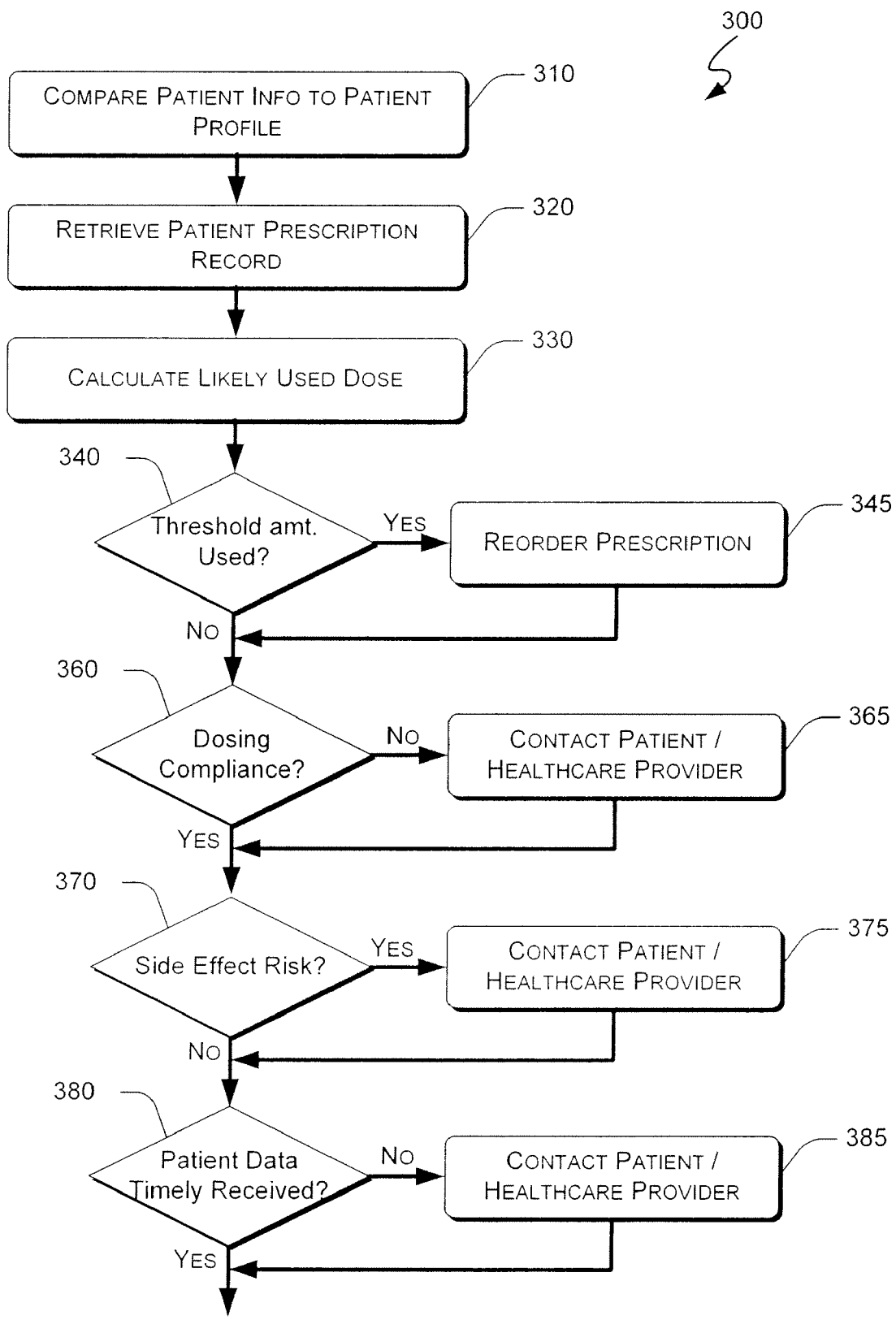
FIG. 3 is a flow diagram of a process according to various aspects of the present invention.

In one exemplary embodiment of the present invention, referring to FIG. 3, the analysis of the patient information (130) includes executing a heuristic algorithm (300). Patient information (such as biometric data, behavioral data, and/or data measured from a medical device) is compared to a profile for the patient (310). The patient profile may be stored in the medical data server and can include the patient's medical record to allow current patient information to be compared to historic readings of the patient's information, such as historic readings stored in the biometric information repository 219. The patient profile can include any other suitable information, such as trends for one or more subsets of the patient's information, trends for one or more disease groups to which the patient belongs, threshold levels for patient information as identified by a healthcare provider for the patient. The patient information can be compared to the patient profile to achieve any suitable purpose, such as to perform a health risk assessment for the patient, identify one or more trends, and to compare the patient information to data stored in a database. Such information may include, without limitation, information on a disease, disease classification data, biological data, biometric data, bioinformatic data, behavioral data, medical device information, and compliance rewards data.

In the exemplary process depicted in FIG. 3, the patient information is analyzed to determine whether new prescriptions need to be ordered for the patient, such as in the case where the patient has used at least a predetermined amount of one or more medications. In this embodiment, a prescription record is retrieved (320) for the patient (e.g.—from the patient profile), and a likely used dose is calculated (330) based on a probable date the prescription was filled, the prescribed dosage rate for the medication, and the date the analysis is being performed. The likely used dose is then compared (340) to a predetermined reorder threshold. If a patient has used at least the predetermined amount of medication, the medication is automatically reordered (345), or alternatively, the patient and/or health care provider is contacted to determine whether the prescriptions should be reordered.

The patient information is also analyzed to determine the degree to which the patient is in compliance (360) with a prescribed medical treatment (e.g. by determining whether the patient has been taking one or more medications on a prescribed schedule, or whether the patient's medical device readings have been within a predetermined range indicating that the patient has been taking prescribed medical treatment on schedule). In an exemplary embodiment, accumulated the patient information that has been received by the medical data server (200) is analyzed for trends and/or analyzed to detect a failure to follow a particular prescribed treatment, and if a failure to follow prescribed treatment is detected, the patient and/or the patient's health care provider is contacted (365) either as a reminder or warning that intervention may be necessary.

An embodiment of the present invention also analyzes whether the patient is at risk from side effects by taking one or more medications (370). Determining whether medication(s) taken by a patient pose a risk of side effects to the patient can be performed in any suitable manner. For example, a medication taken by the patient can be analyzed to determine whether it will interact with at least one of: a second medication taken by the patient; a newly prescribed medication; an over-the-counter medication; an herbal supplement; a vitamin; and an edible food or beverage. Additionally, a cytochrome P450 metabolic profile of a first medication taken by the patient and a cytochrome P450 metabolic profile of a second substance to be administered to the patient may be compared to determine that: metabolism via a substrate of the cytochrome P450 metabolic profile of the first medication is likely to be inhibited by the second substance; metabolism via a substrate of the cytochrome P450 metabolic profile of the first medication is likely to be induced by the second substance; metabolism via a substrate of the cytochrome P450 metabolic profile of the first medication is likely to be competitively inhibited by the second substance; metabolism via a substrate of the cytochrome P450 metabolic profile of the second substance is likely to be inhibited by the first medication; metabolism via a substrate of the cytochrome P450 metabolic profile of the second substance is likely to be induced by the first medication; metabolism via a substrate of the cytochrome P450 metabolic profile of the first medication is likely to be slower than a population metabolic rate based on a genetic profile of the patient; metabolism via a substrate of the cytochrome P450 metabolic profile of the first medication is likely to be faster than a population metabolic rate based on a genetic profile of the patient; and combinations thereof. If a risk of side effect is detected by any method, the patient and/or patient's health care provider is contacted (375) to provide notification that intervention may be required or prescriptions may need to be altered.

The exemplary process depicted in FIG. 3 further includes determining if the patient information has been received within a predetermined interval (380). A failure to receive patient information at a predetermined interval can be indicative of noncompliance with a treatment regimen, failure or malfunction of one or more devices providing the patient information, one or more medical devices or intermediate devices being out of broadcast range, and/or a medical emergency. In one embodiment, patient information is analyzed by the medical data server (200) and compared to a predetermined threshold for expected medical data monitoring schedules. For example, but not by way of limitation, a diabetic patient may be instructed to use a glucose meter to take readings three times a day, and thus, patient information received in the medical data server (200) is compared to the expected 3 times per day monitoring requirement, and if the medical information received does not satisfy the predetermined monitoring requirement within a predetermined margin of error, action is taken such as contacting the patient, and/or the patient's health care provider (385).

Report Formatting

In the exemplary method according to an aspect of the present invention depicted in FIG. 1, a report is formatted based on the patient information and the patient condition (135). The report can include some or all of the patient information, as well as any other information useful to the patient or another user (such as a healthcare provider). Multiple reports can be formatted to include any desired amount of information. For example, in the case where the patient information includes data from a glucose meter, multiple reports may be formatted to each include a single glucose reading, or a single message could be formatted to include the last ten glucose readings taken by the meter. The report can provide additional information (e.g. to show comparisons between the patient information and other data), such as, without limitation, information on a disease, disease classification data, biological data, biometric data, bioinformatic data, behavioral data, medical device information, and compliance rewards data. The report can include any other desired information, such as information regarding the patient condition and other results of analyzing the patient information.

The report can include any other desired data from any suitable source. For example, patient information that includes real-time data from a medical device may be included in a report along with previously-received patient information by the same medical device. The report (in whole or in part) may be encrypted to protect the contents of the message from unintended viewers and/or the privacy of the patient being monitored, as well as to comply with government regulations, such as Health Insurance Portability and Accountability Act (HIPAA) regulations.

The report provides information to a recipient in a format the recipient can recognize and utilize. The report can thus be formatted to only include portions of the medical device data needed by the particular recipient. Multiple reports can be formatted for multiple recipients based on the identity of the recipient. For example, a report formatted for a doctor or nurse may include information about a patient's treatment regimen, medications, behavioral data, biometric information, diagnostic information regarding one or more medical devices used by the patient, and other detailed information relating to the health and wellness of the patient. A report formatted for a call center operator, on the other hand, may only include general information regarding the patient to protect the patient's privacy and help expedite assistance from a call center operator who only needs the general information to advise the patient and/or to route the client to a qualified doctor or nurse.

The report can be of desired format. For example, the message can be included in a file having a tokenized format such as standard ASCII text format, or any other suitable standardized file format, such as an MS Word document, MS Excel file, Adobe PDF file, or binary picture file (JPEG, bitmap, etc.). The data within such a file can be ordered in any manner and have any suitable delimiters, notations, or other features. For example, a list of multiple glucose level readings in a text file report could be provided chronologically by when the readings were taken, with comma or tab delimiters to denote the start and end of each reading. The message may also have a unique and/or propriety format.

The format of the report can also be based on the method by which the report is transmitted to a recipient, as well as on the identity of the recipient of the report. For example, where the patient information is transmitted to the recipient using a wireless mobile telephone such as a cellular phone, the report can be formatted as an SMS text message. Similarly, the report may be formatted as an XML record, email, and/or facsimile. The report can include multiple formats and/or multiple reports may be formatted having different formats for transmission in a variety of methods or to a variety of recipients.

User Communication

The exemplary process depicted in FIG. 1 provides for bidirectional communication with one or more users. A user can be any device, system, process, operator, or other entity capable of providing and receiving information with systems and methods of the present invention. For example, a user may include a doctor, nurse, system administrator, or other healthcare provider. A user may also include a computer system controlled by software and/or hardware, such as a mobile computing device. In one exemplary embodiment of the present invention, a formatted report including patient information from one medical device can be provided to a second medical device. This allows medical devices to share information with one another through systems and methods for remote patient monitoring according to the present invention. In this exemplary embodiment, the patient information can be received directly from the medical device (270), or through one or more intermediary devices. Similarly, the report can be transmitted directly to the second device, or via one or more intermediary devices. The patient information can also be received from one medical device through an intermediary device, and transmitted to a second medical device through the same intermediary device. This would allow a single intermediary device (such as a router, hub, mobile computing device, medical data interchange device, medical data translator, or other device) to allow data from multiple medical devices to be provided to a medical data server or other system implementing methods of the present invention, as well as amongst the different medical devices, even where the medical devices do not share a common communications format or protocol.

Any suitable information can be provided to a user, such as one or more reports based on the patient information and the condition of the patient. The report can be provided to a user by request, or automatically upon the occurrence of an event. For example, a report including data for a patient may be provided automatically to a user within a predetermined amount of time after the medical data server (200) receives patient information, or at a predetermined interval. In this way, patient information can be streamed to a doctor, nurse, or other user to allow the user to periodically monitor the health and wellness of the patient over time. The report can also be automatically provided to a user when the report includes a predetermined amount of data, or automatically provided when a difference between the time stamp for one set of data in the report and a time stamp for another set of data in the report exceeds a predetermined duration.

The formatted report and other information can be provided selectively to one or more recipients based on the patient information, patient condition, a relation between the recipient(s) and the patient, and/or whether the one or more recipients are authorized to receive the report. In this way, the scope and content of patient information and other data disseminated by systems and methods of the present invention can be controlled. For example, doctors and nurses who need detailed information for a patient (such as specific readings from a medical device) can have such information provided to them based on their status as the primary caregivers for the patient. On the other hand, call center operators, insurance agents, and other users without the need (or access privileges) to such detailed and/or sensitive information can be provided modified or redacted patient information. The selective providing of data to users can be automated and performed according to rules (such as from the rules database 228). The formatted report and other information can be provided to a user at any desired interval or set of intervals, according to any condition(s), and/or upon the occurrence of any other suitable event.

Information provided to a user may be in any format and configuration. For example, a report based on patient information and a patient condition may be provided to a user using a web page layout, a spreadsheet, a facsimile, an email, an SMS text message, and/or an HIPAA-compliant format.

Similarly, the user can communicate any suitable information to a system implementing methods in accordance with the present invention. For example, a user (such as a doctor, nurse or other healthcare provider) may provide one or more predetermined threshold conditions for the patient information. When patient information is received, it is compared to the threshold conditions. The formatted report may include the result of the comparison, and can be automatically provided to the user (or other users) when the patient information conforms (or fails to conform) to one or more of the threshold conditions.

Other information from a user can be processed and handled in any appropriate manner. For example, commands or instructions from the user regarding the receipt of patient information, analysis of the patient information, formatting of reports, or other functions performed in accordance with the present invention may be used to alter or halt such functions.

Communication with a user can be performed in any manner. For example, information such as the formatted report can be provided to one or more users using a web interface, an electronic mail message, a facsimile, an audio transmission, a voice message, a text message, and/or a video transmission. Information can be provided through an interactive voice response (IVR) system, a mobile computing device, a mobile telecommunications device, a computer system connected to a network, or by a human operator. Similarly, users can communicate information to systems operating in accordance with the present invention in any appropriate manner, including the methods listed above.

Patient Communication

The exemplary process depicted in FIG. 1 provides for bidirectional communication (145) with one or more patients. Any suitable information can be provided to a patient, such as one or more reports based on the patient information and the condition of the patient as can be provided to other users of systems for remote patient monitoring. The report can be provided to the patient upon request by the patient or healthcare provider, automatically upon the occurrence of an event, at predetermined intervals, and/or based on one or more conditions just as reports can be provided to users as discussed previously. Such contact can be made automatically, such as through an interactive voice response (IVR) system, or by a nurse, doctor, call center operator, or other healthcare representative/associate. While a patient may be allowed to communicate with a systems of the present invention as a user as discussed above, some communications are particularly appropriate with patients as opposed to other users of the system.

For example, the patient can be contacted to provide information, instructions, alerts, warnings, and to respond to questions regarding the patient's own health and wellness. The patient can be contacted when a patient condition based on the patient's information satisfies a threshold condition. Contact with the patient can be made in accordance with any suitable condition, such as a condition that represents a present harmful patient condition and/or a potential future harmful condition. In this manner, systems and methods for remote patient monitoring according to the present invention can be used to quickly alert a patient to a harmful condition, instruct the patient to seek treatment, take a medication, implement a treatment regimen, or take other actions to address presently-occurring medical emergencies and avoid impending emergencies.

Contact with the patient may be made after an analysis of the patient information. For example, current information for a patient may be compared to the medical record for the patient and/or the patient's condition. The patient may then be contacted if an abnormality is detected or the comparison satisfies a predetermined threshold condition (such as a blood pressure rate specified by the patient's doctor). The patient can also be contacted to verify the patient is in compliance with a prescribed medical treatment, such as to verify the patient is taking a medication.

The patient may also be contacted based on the timely (or untimely) receipt of patient information. For example, the patient may be contacted if patient information is not received for a predetermined interval or according to a predetermined schedule. Such failure could be the result of a failure by the patient to adhere to a prescribed medical treatment, such as the case where a diabetic patient is required to use a glucose meter at set intervals, and where the glucose meter provides the patient's blood sugar readings to a medical data server or wellness monitoring system implementing methods in accordance with the present invention.

In the case where the patient is a child, the patient information may be sent to a parent or other responsible person. For example, a child, who is type 1 diabetic, may be required to take readings at both her school during the day and at home. When the child takes a reading at school, the reading will be automatically sent to one of her parent's cell phones, so the parent can make sure the child is taking her readings on a timely basis and be aware of the quantitative value.

Contact with the patient can be used to provide the patient with a reward if the patient's level of compliance with a treatment regimen or other program meets or exceeds a predetermined threshold. Conversely, the patient can be contacted to recommend further treatment where the patient's level of compliance does not meet a predetermined threshold. The patient may also be contacted to provide a list of information and/or questions to the patient. The list may be created by a doctor, nurse, or other healthcare provider. The patient provides responses to the questions to provide additional patient information that can be processed by a remote patient monitoring system and/or forwarded to a healthcare provider.

Information provided to a patient may be in any format and configuration. For example, a report based on patient information and a patient condition may be provided to a patient using a web page layout, a spreadsheet, a facsimile, an email, an SMS text message, and/or an HIPAA-compliant format. Communication with a patient can be performed in any manner. For example, information such as the formatted report can be provided to a patient using a web interface, an electronic mail message, a facsimile, an audio transmission, a voice message, a text message, and/or a video transmission. Information can be provided through an interactive voice response (IVR) system, a mobile computing device, a mobile telecommunications device, a computer system connected to a network, or by a human operator. Similarly, patients can communicate information (such as responses to questions or other data) to systems operating in accordance with the present invention in any appropriate manner, including the methods listed above. Systems and methods for remote patient monitoring may be configured to accommodate the simultaneous communication with multiple patients.

A patient can communicate any suitable information to a system implementing methods in accordance with the present invention. In one exemplary embodiment of the present invention, receiving a communication from a patient identifies the patient based at least partially on an identifier associated with the communication and route the communication to an appropriate user. An identifier can be the patient's name, a phone number (such as identified through caller identification data obtained through a public switched telephone network or mobile telephone network), an email address, a MAC address, an IP address, and/or any other identifier associated with the patient. The communication can be routed to any suitable user, such as a disease management vendor, an educational institution, a government entity, a healthcare provider, or other suitable recipient for the communication. The communication can be routed to a user based on any suitable criteria or conditions, such as the status, capability, and location of the user. For example, a patient contacting a system for remote patient monitoring via telephone in accordance with the present invention can be identified by the incoming phone number and automatically routed to a doctor or nurse caring for the patient. The doctor or nurse can also be provided with information for the patient, a copy of the patient's medical history and/or the patient's condition. Patient information provided to users in this manner may include any suitable data, such as data measured from one or more medical devices. In this way, systems and methods for remote patient monitoring according to the present invention provide quick and efficient routing of patients to caregivers so that the patient need not endure a long (and potentially dangerous) wait to speak to a qualified caregiver. This allows more patients to be serviced in less time, and with fewer delays.

Data Storage

The patient information and other data can be stored (155) in any suitable manner, such as by using one or more memory storage devices, and one or more databases. Any portion or amount of patient information, patient condition, formatted report, or other forms of information received or generated by the medical data server or other system implementing methods according to the present invention may be stored for any length of time. The data can be stored in any configuration. For example, the patient information, patient condition and formatted report may all be stored as part of a medical record for the patient. The medical record can be processed using systems and methods of the present invention to perform a health risk assessment for the patient, identify one or more trends for the patient or among multiple patients, compare medical record information entries in a database, or for other suitable purposes. Database information used in conjunction with the processing of the medical record may include, without limitation, information on a disease, disease classification data, biological data, biometric data, bioinformatic data, behavioral data, medical device information, and compliance rewards data.

Stored data such as the patient information, the patient condition, and the report may be assigned one or more classifications according to a hierarchy. The classifications can be used for any suitable purpose, such as to restrict access by users according to the hierarchy and an identification associated with the user. For example, some types of sensitive patient information may be classified under a hierarchy that restricts the access to the sensitive information only to a patient's doctor. Other users of the remote patient monitoring system (such as a call center operator) would be denied access. Identification of the user can be determined in any manner, such as through a username, passcode, or other identifier associated with the user.

Patient information and/or other data may be stored for a predefined period of time and/or until an event occurs. For example, in one embodiment of the present invention the patient information is stored in a database until a report has been transmitted to a user. In another embodiment, data is stored by the medical data server until a predetermined data transmission record size (i.e. of the formatted report) has been reached, so as to reduce communication charges that may accrue during transmission. In yet another embodiment, the medical data server stores the data until an acknowledgment or command from a user is received, where the acknowledgment or command indicates that the stored data has been received by the user and should be deleted.

Additional Processing

Systems and methods for remote patient monitoring according to various aspects of the present invention may perform (160) appropriate additional processing. For example, methods may be implemented to ensure a remote patient monitoring system is compliant with governmental regulations, such as Health Insurance Portability and Accountability Act (HIPPA) regulations. For example, an audit record may be created that includes data fields indicative of the compliance or non-compliance with such regulatory standards. The audit record can be produced and reviewed by auditors to verify that systems and methods for remote patient monitoring are acting in accordance with such regulations.

Figure 4:
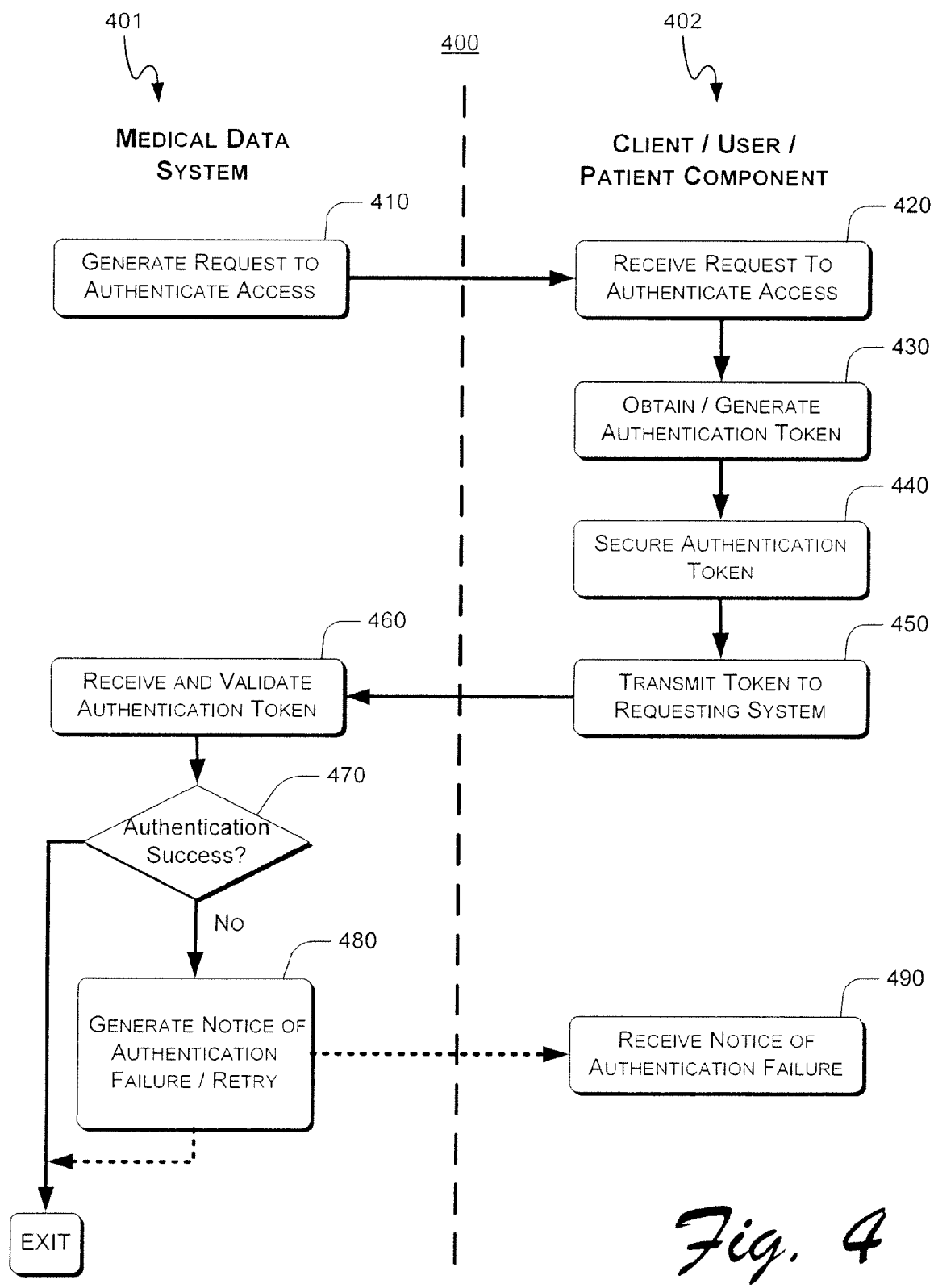
FIG. 4 is a flow diagram of an exemplary process for authenticating access to a system component of the present invention

In another embodiment, in regards to the methods described in regards to FIG. 1, it is desirable to ensure that a party attempting to interface with a system such as a medical data server is actually the party believed to be authorized to do so. Turning to FIG. 4, an embodiment is provided that illustrates a method to authenticate user access to the medical data server. A medical data system component 401 such as a medical data server (FIG. 2, 200) generates 410 a request to authenticate access, either on its own accord or as a result of a message received by an alleged patient who is enrolled in the medical service provided by the medical data server. The medical data system 401 then sends a request to authenticate access to a user component 402 of the present invention associated with the client, user, or health care provider. The user component 402 then receives 420 the request to authenticate access, and generates 430 an authentication token.

In various embodiments, authentication tokens may comprise either simple or complex text strings or data values indicating an account number or other patient identifier that can be matched against an internal patient database by the medical data server. Alternatively, authentication tokens may comprise encoded passwords or other indicia that assert that the entity for whom authentication is requested is genuine. Generation of an authentication token may be accomplished using alternative methods such as entry of a patient identifier, PIN, or password by a patient or healthcare provider after being prompted to do so. Alternatively, a biometric measurement of the patient or healthcare provider could be obtained and the measurement rendered into a digital representation. Once generated, for security purposes the authorization token may be secured 440 by encrypting the token, digesting and encrypting the digest of the token, or cryptographically hashing the token before transmission to the requesting entity such as the medical data system 401 or server. As discussed above in regards to the abovementioned command authentication, in one embodiment, when authentication tokens are created, the originating component of the token may create a certification of validity through at least one of the following methods: (1) encrypting the token with a private key associated with the token originator; (2) encrypting the token with a public key associated with the token requester or destination; (3) generating a digest of the token (through a method such as a hashing algorithm discussed above) and optionally encrypting the hashed digest with the token originator's private key, or (4) providing an authentication code as at least part of the token (such as a cryptographically hashed password) that may be is compared to previously stored values. Then, the secured authentication token is transmitted 450, and when a medical data system component 401 receives the token along with any encrypted or cleartext certification data, the component may determine the access is valid by (1) attempting to decrypt an encrypted token with the alleged originator's public key; (2) attempting to decrypt an encrypted token with the alleged originator's public key; (3) attempting to decrypt an encrypted digest with the alleged originator's public key, and comparing the result to a hashed value of the token, pin, code, or password, or (4) comparing a cryptographically hashed password for the alleged originator to known pre-stored values, and if a match is found, authorization is granted.

The medical data system component 401 then receives 460 and analyzes 470 the validity of the authentication token as described above. If examination of the authentication token provides that the token is authentic, such as by comparing the analyzed token data to known, pre-stored values such as the patient or the patient's health care provider's pre-stored hashed password or other identity datum, then access is successful and the process terminates. After analyzing the authentication token or a message containing or associated with the token, the medical data system may determine that access is either permitted or denied, and may communicate 480 this status to the originator of the authentication token 402 who then receives notice of the failure 490. At that point, the system may repeat the process 400, allowing the token originator to attempt access again.

Command Transmission

Returning to FIG. 1, the medical data server 200 or other system performing methods in accordance with the present invention may transmit a command (165). The command can be received by a medical device, an intermediary device in communication with the medical device or patient, and/or or any other suitable recipient. Any number of commands of any type may be transmitted by the medical data server. The command can be transmitted using the same variety of wired and wireless methods discussed previously for the transmittal of the formatted report and for communication with a user or patient. The command need not be transmitted using the same communication method with which the patient information is transmitted to the medical data server.

In one embodiment of the present invention, for example, the medical data server (200) issues a command to reconfigure a software application operating on an intermediary device receiving patient information from a medical device and retransmitting the patient information to the medical data server 200. In another embodiment, the medical data server 200 issues one or more commands to control the functionality of the medical device. In yet another embodiment, the medical data server 200 issues one or more commands to request that a public encryption key corresponding to the patient using a medical device be forwarded to the medical data server, or that a device associated with the present invention receive a public encryption key corresponding to an intended recipient such as a particular health care service provider or other known destination such as the medical data server.

The commands need not be sent directly to a device they are intended to control. For example, a command could be transmitted to an intermediary device, which in turn retransmits it (unmodified) to the medical device to be controlled. Alternatively, the intermediary device could receive a command from the medical server, analyze it, and then transmit an appropriately formatted command tailored to the specific medical device to be controlled. In this manner, the medical data server need not be required to generate a command for each and every specific device it wishes to control, as it can send a command appropriate to a class of devices (i.e. glucose meters) and the intermediary device will appropriately translate the command to control the medical device. The commands from the medical data server can initiate/run diagnostic programs, download data, request the patient's public encryption key, download the intended recipient's public encryption key, and perform any other suitable function on the intermediary device, medical device, or other devices operating in conjunction with systems and methods of the present invention.

A command from a medical data server can be in any appropriate format and may include any suitable information. For example, a command may include data received from one medical device to be delivered to another medical device through an intermediary device. In this manner, a variety of medical devices can share data whether they are in direct communication with the medical data translator 200 or not.

In any system where commands can be sent remotely, security is always a concern, especially when a wireless implementation may provide an entry vector for an interloper to gain access to components, observe confidential patient information, and control health-sensitive components such as pacemakers and insulin pumps. In any digital data network, it is also possible that commands intended for one recipient may be misrouted to a patient or health care provider that was not the intended recipient of the command. There are, however, a number of methods to provide for enhanced security in a remote command system while still allowing flexibility and minimal obtrusiveness.

In one embodiment, a command received by any of the components in FIG. 2 may be authenticated before the command is either acted upon by the destination component, or forwarded to another component in the system. Authentication may be directed to determining (1) whether the command came from a trusted or authorized source and (2) that the recipient is actually the intended recipient of the command. In one implementation, source command authentication is achieved by determining whether the origin of the command is a trusted component or server, and one way to accomplish this determination is analyzing whether a command is properly digitally signed by the originator, or some other authentication information is provided that assures the recipient component that the message or command is authentic and the recipient component is actually the intended recipient. In an alternate implementation, destination command authentication is accommodated by examining the contents of the message or an authorization code to determine the intended recipient, or alternatively decrypting the command or a portion of the command to verify the intended recipient.

In one embodiment, when commands are created by a command originator, the originator provides for a means to verify the authenticity and/or validity of the command by at least one of the following methods: (1) encrypting the command with a private key of the command originator; (2) generating a digest of the command (through a method such as a hashing algorithm discussed above) and optionally encrypting the hashed digest with the command originator's private key, or (3) utilizing a symmetric encryption scheme providing an authentication code (such as a cryptographically hashed password) that is compared to previously stored values. Then, when a system component receives the command along with any encrypted or cleartext certification data, the component may determine the command is valid by (1) attempting to decrypt an encrypted command message with the alleged originator's public key, (2) attempting to decrypt an encrypted digest with the alleged originator's public key, and comparing the result to a hashed value of the command, or (3) comparing a cryptographically hashed password for the alleged originator to known pre-stored values, and if a match is found, authorization is granted. As an additional step, if the command were optionally encrypted using the intended patient/provider's public key, then only the recipient is capable of decrypting the command, ensuring that only the truly intended patient's health-care devices were being issued commands, and not an unintended third party. For example, in one embodiment, authenticating the command comprises decrypting at least part of the command using at least one of:

a public key associated with the medical data server; a private key associated with a user of the medical device; and a private key associated with the medical device.

Exemplary System

An exemplary system for remotely monitoring the wellness of a patient in conjunction with the present invention is depicted in FIG. 2. This system may be used in conjunction with the method described in FIGS. 1, 3, and 4, as well as with any subset or combination of the elements thereof. The system shown in FIG. 2 may also be used in conjunction with any other suitable embodiments of systems and methods for remote patient monitoring according to an aspect of the present invention.

The exemplary system for remotely monitoring the health and wellness of a patient depicted in FIG. 2 comprises a medical data server 200 that includes a system processor and application server 202 in communication (such as through a bus) with a system interface 205, Behavioral Information Repository 213, Biometric Information Repository 219, Knowledge Base 222, Biological Information Repository 225, memory 226, Rules Database 228, Bioinformatics Information Repository 231, Medical Data Capture Repository 233, and Rewards Database 235.

System Processor and Application Server 202

The system processor and application server 202 retrieves and executes instructions stored in the memory 226 to control the operation of the medical data server 200. Any number and type of conventional computer, computer system, computer network, computer workstation, minicomputer, mainframe computer, or computer processor, such as an integrated circuit microprocessor or microcontroller can be used in conjunction with the present invention. As those skilled in the art will appreciate, any computer used in accordance with aspects of the present invention may include an operating system (e.g., Windows NT, 95/98/2000/XP/Vista, OS2, UNIX, Linux, Solaris, MacOS, etc.) as well as various conventional support software and drivers typically associated with computers. In certain embodiments, dedicated health care-related applications may be entirely or partially served or executed by the system processor 200 in performing methods or processes of the present invention.

Memory 220

The exemplary system in FIG. 2 includes a memory 226. The memory 226 stores instructions, patient information, patient conditions, patient medical history, and any other suitable information. A memory operating in conjunction with the present invention may include any combination of different memory storage devices, such as hard drives, random access memory (RAM), read only memory (ROM), FLASH memory, or any other type of volatile and/or non-volatile memory. Systems and methods for remote patient monitoring may also store and retrieve data from one or more databases, such as the Behavioral Information Repository 213, Biometric Information Repository 219, Knowledge Base 222, Biological Information Repository 225, Rules Database 228, Bioinformatics Information Repository 231, Medical Data Capture Repository 233, and Rewards Database 235 depicted in FIG. 2.

The exemplary system depicted in FIG. 2 includes a biological information repository 225, biometric information repository 219, and bioinformatics information repository 231 for storage and retrieval of a patient's biological data, biometric data, and bioinformatics data respectively. In an exemplary embodiment, this data is generated by one or more medical devices 250 and transmitted to the application server 202. The biological data is available for access by a user 240 or patient through the system interface 205, and may be used in the analysis of the patient information. Similarly, the bioinformatics information repository is configured to support the analysis of the biological and behavioral data received from patients.

The medical data capture repository 233 may be used to store medical data from any suitable source, such as from one or more medical devices used by a patient. The medical data capture repository 233 can include data for individual patients (and identified as such) or general data from groups of patients. Such information can be used to diagnose trends in a population of patients or identify a condition for a patient exhibiting particular symptoms.

The behavioral information repository 213 allows for the storage and retrieval of a patient's behavioral data. In an exemplary embodiment, behavioral data is captured from a patient through a variety of mechanisms (IVR, Text Messages, et al), transmitted to the application server 202, and stored in the repository 213. In some embodiments, the behavioral information is available to authorized entities through the system interface 205.

The knowledge base 222 is configured to store information about diseases and disease classifications. In exemplary embodiments, the information is used by various subsystems in the invention when communicating with the patient or users (such as disease management vendors and healthcare providers). For example, an Interactive Voice Response ("IVR") service included in the patient interface 207 may interact with the patient 270 in gathering behavioral information as a function of the information provided by the knowledge base 222.

The rules database 228 is configured to store and retrieve business rules. The rules are executed based on the current content of other databases (for example, a patient's biological and behavioral data, patients' disease thresholds, disease type trends, geographical medical data, and results from previously-prescribed actions). The patient management rules are configurable and maintainable by the disease management entities and healthcare providers through the system interface 205.

The rewards database 235 is configured to store information related to motivating patients to alter their health-related behavior, and record the result of behavior-changing programs. Information from the rewards database 235 may be used when recommendations on behavioral changes are required by a user, such as a doctor, nurse, or call center agent.

System Interface 205

The medical data server includes a system interface 205 comprising a patient interface 207 and a user interface 209. Both the patient interface 207 and user interface 209 may include any number of human operators, computer systems, mobile telephones, mobile computing devices, interactive voice response (IVR) systems, and any other suitable system and device for communicating with a patient 270 or user 240. In this exemplary embodiment, the system interface 205 is configured to allow the direct communication (through any suitable wired or wireless communication connection) between the medical data server 200 and a patient 270, medical device 250, and/or intermediary device 260. Alternately, the medical data server 200 may communicate with an intermediary device 260, wherein the intermediary device 260 receives patient information from a medical device 250 through a wireless or wired connection 258. In various embodiments, therefore, the medical device 250 may communicate either directly to the system interface 205 or to the system interface 250 through the intermediary device 260.

The system interface 205 may additionally include any number of input devices (not shown). For example, the system interface may include a keyboard, mouse, touch pad, touch screen, alphanumeric keypad, voice recognition system, or other input device to allow a user 240 or patient 270 to provide instructions and information to the medical data server 200. Similarly, the system interface 205 may include any number of suitable output devices (not shown), such as a monitor, speaker, printer, or other device.

Any type of information may be communicated through the system interface 205 by a user or patient as discussed previously, such as the biological, biometric, or behavioral information for one or more patients. Information provided or received by the system interface 205 may be in any appropriate format. For example, an output device providing information to a user visually may provide patient information in the form of a series of measurements from different medical devices in a spreadsheet with headers indicating the source of the measurements. The system interface 205 can provide information in any number of desired languages, regardless of whether the information is provided audibly or visually.

Various features of the system interface 205 can be implemented in hardware, software, or a combination of the two. The system interface 250 can also provide/receive information to a user in a machine-readable format. The system interface 205 may interface with any suitable system or device, such as a thumb drive, memory stick, portable hard drive, an external computer system, or other USB-compatible device. The system interface 205 can be configured to send, receive, and process machine-readable data can in any standard format (such as a MS Word document, Adobe PDF file, ASCII text file, JPEG, or other standard format) as well as any proprietary format. Machine-readable data to or from the system interface may also be encrypted to protect the data from unintended recipients and/or improper use, as well as to comply with governmental regulations (such as HIPAA). Any other feature may be utilized in conjunction with the system interface 205 to allow a human or non-human user to interact with the medical data server 200.

Security Measures

Systems and devices operating in accordance with aspects of the present invention may implement one or more security measures to protect data, restrict access, or provide any other desired security feature. For example, any device operating in conjunction with the present invention may encrypt transmitted data and/or protect data stored within the device itself. Such security measures may be implemented using hardware, software, or a combination thereof. Any method of data encryption or protection may be utilized in conjunction with the present invention, such as public/private keyed encryption systems, data scrambling methods, hardware and software firewalls, tamper-resistant or tamper-responsive memory storage devices or any other method or technique for protecting data. Similarly, passwords, biometrics, access cards or other hardware, or any other system, device, and/or method may be employed to restrict access to any device operating in conjunction with the present invention.

The particular implementations shown and described above are illustrative of the invention and its best mode and are not intended to otherwise limit the scope of the present invention in any way. Indeed, for the sake of brevity, conventional data storage, data transmission, and other functional aspects of the systems may not be described in detail. Methods illustrated in the various figures may include more, fewer, or other steps. Additionally, steps may be performed in any suitable order without departing from the scope of the invention. Furthermore, the connecting lines shown in the various figures are intended to represent exemplary functional relationships and/or physical couplings between the various elements. Many alternative or additional functional relationships or physical connections may be present in a practical system.

Changes and modifications may be made to the disclosed embodiments without departing from the scope of the present invention. These and other changes or modifications are intended to be included within the scope of the present invention, as expressed in the following claims.

What is claimed is:

1. A method comprising:
   receiving patient information related to one or more patients from a plurality of medical devices comprising a plurality of medical device types, wherein at least one of the medical devices uses a different communications protocol from the other of the plurality of medical devices, the patient information received through one or more of a plurality of intermediary devices, wherein each of the plurality of intermediary devices is capable of communicating with each of the plurality of medical devices;
   at least some of the plurality of intermediary devices communicating with one or more of the plurality of medical devices, wherein at least one of the communications uses a different communications protocol from the other communications;
   wherein each of the plurality of intermediary devices that communicates with one or more of the plurality of medical devices:
      automatically detects, based on a voltage of a signal received from the medical device, a communication protocol used by the medical device;
      automatically configures a medical device interface of a plurality of medical device interfaces to communicate with the medical device using the detected communication protocol, wherein each medical device interface is configured to receive patient data via a wired connection from a plurality of different medical devices; and
   transmits the patient information received from each of the medical devices to a processor;
   analyzing by the processor the patient information received from each of the plurality of medical devices and for each of the one or more patients to identify a condition for each of the one or more patients;
   formatting a report for each of the one or more patients based on the patient information and the patient condition for each patient; and
   providing each of the reports to a recipient, wherein each of the reports is provided to the recipient automatically when a difference between a time stamp for a first set of data in the report and a time stamp for a second set of data in the report exceeds a predetermined duration.

2. The method of claim 1, wherein the report is provided to the recipient within a predetermined amount of time of receiving the patient information.

3. The method of claim 1, further comprising:
   receiving one or more predetermined threshold conditions for the patient information from a user;
   comparing the patient information to the one or more predetermined threshold conditions; and
   providing the formatted report to the user when the patient information conforms to at least one of the one or more predetermined threshold conditions.

4. The method of claim 1, further comprising transmitting the formatted report to one or more recipients using at least one of a web interface, an electronic mail message, a facsimile, an audio transmission, a voice message, a text message, and a video transmission, wherein transmitting the formatted report to one or more recipients includes at least one of:

transmitting the report when one or more recipients submit a request for the report;
   transmitting the report automatically at a predetermined interval;
   transmitting the report automatically when the report includes a predetermined amount of data; and
   selecting the one or more recipients from a plurality of possible recipients.

5. The method of claim 4, wherein selecting the one or more recipients from the plurality of possible recipients is based on at least one of:

the patient information;
   the patient condition;
   a relation between the one or more recipients and the patient; and
   whether the one or more recipients are authorized to receive the report.

6. The method of claim 1, wherein the patient information is generated by a first medical device, the method further comprising formatting a message regarding the patient information for transmission to a second medical device.

7. The method of claim 6, wherein the patient information is received through an intermediary device in communication with the first medical device.

8. The method of claim 6, wherein the patient information is transmitted to the second medical device through an intermediary device in communication with the second medical device.

9. The method of claim 6, wherein an intermediary device is in communication with both the first medical device and second medical device, and wherein the patient information is received from the first medical device through the intermediary device and transmitted to the second medical device through the intermediary device.

10. The method of claim 1, wherein the patient information is received by at least one of an interactive voice response (IVR) system, a mobile computing device, a mobile telecommunication device, a computer system connected to a network, and a human operator.

11. The method of claim 1, further comprising authorizing a service, wherein authorizing a service includes:

obtaining an identifier for the patient; and
   retrieving, based on the patient identifier, one or more available authorized services.

12. The method of claim 1, wherein the patient information includes information regarding a plurality of patients measured by the medical device.

13. The method of claim 12, wherein the patient information includes a patient identifier for each of the plurality of patients.

14. A wellness monitoring system comprising:

a processor;
   a patient interface;
   a plurality of medical devices comprising a plurality of medical device types, wherein at least one of the medical devices uses a different communications protocol from the other of the plurality of medical devices;
   a plurality of intermediary devices, wherein each intermediary device can communicate with each of the communications protocols utilized by the plurality of medical devices, wherein each of the plurality of intermediary devices that communicates with one or more of the plurality of medical devices:
      automatically detects, based on a voltage of a signal received from the medical device, a communication protocol used by the medical device; and
      automatically configures a medical device interface of a plurality of medical device interfaces for the intermediary device to communicate with the medical device using the detected communication protocol, wherein each medical device interface is configured to receive patient data via a wired connection from a plurality of different medical devices;
   a user interface; and
   a memory coupled to the processor and storing instructions that, when executed by the processor, cause the processor to:
      receive patient information using the patient interface, the patient information related to one or more patients, from the plurality of medical devices, the patient information received through one or more of the plurality of intermediary devices;
      analyze the patient information from each of the plurality of medical devices and for each of the one or more patients to identify a condition for each of the one or more patients;
      format a report for each of the one or more patients based on the patient information and the patient condition for each patient; and
      provide each of the reports to one or more users using the user interface, wherein the report is provided to the one or more users automatically when a difference between a time stamp for a first set of data in the report and a time stamp for a second set of data in the report exceeds a predetermined duration.

15. The system of claim 14, wherein the memory further stores instructions that, when executed by the processor, cause the processor to:

receive one or more predetermined threshold conditions for the patient information for each of the one or more patients from a user through the user interface;
   compare the patient information for each of the one or more patients to the one or more predetermined threshold conditions for each of the one or more patients; and
   provide the formatted report to the user using the user interface when the patient information conforms to at least one of the one or more predetermined threshold conditions for that particular patient.

16. The system of claim 14, wherein the wellness monitoring system is further configured to transmit the formatted report to one or more recipients through the user interface using at least one of a web interface, an electronic mail message, a facsimile, an audio transmission, a voice message, a text message, and a video transmission, wherein the transmission of the formatted report to one or more recipients includes at least one of:

transmitting the report when one or more recipients submit a request for the report through the user interface;
   transmitting the report automatically at a predetermined interval;
   transmitting the report automatically when the report includes a predetermined amount of data; and
   selecting the one or more recipients from a plurality of possible recipients.

17. The system of claim 16, wherein the selection of the one or more recipients from the plurality of possible recipients is based on at least one of:

the patient information;
   the patient condition;

a relation between the one or more recipients and the patient; and whether the one or more recipients are authorized to receive the report.

18. The system of claim 14, wherein the patient information is generated by a first medical device, the wellness monitoring system is further configured to format a message regarding the patient information for transmission to a second medical device through at least one of the patient interface and the user interface.

19. The system of claim 18, wherein the patient information is received through an intermediary device in communication with the first medical device.

20. The system of claim 18, wherein the patient information is transmitted to the second medical device through an intermediary device in communication with the second medical device.

21. The system of claim 18, wherein an intermediary device is in communication with both the first medical device and second medical device, and wherein the patient information is received from the first medical device through the intermediary device and transmitted to the second medical device through the intermediary device.

22. The system of claim 14, wherein the patient interface includes at least one of an interactive voice response (IVR) system, a mobile computing device, a mobile telecommunication device, a computer system connected to a network, and a human operator.

23. The system of claim 14, wherein the memory further stores instructions that, when executed by the processor, cause the processor to authorize a service, wherein authorizing a service includes:

obtaining an identifier for the patient; and retrieving, based on the patient identifier, one or more available authorized services.

24. The system of claim 14, wherein the patient information includes information regarding a plurality of patients measured by the medical device.

25. The system of claim 24, wherein the patient information includes a patient identifier for each of the plurality of patients.

* * * * *